(12) United States Patent
Engelhardt

(10) Patent No.: US 6,975,394 B2
(45) Date of Patent: Dec. 13, 2005

(54) METHOD AND APPARATUS FOR MEASURING THE LIFETIME OF AN EXCITED STATE IN A SPECIMEN

(75) Inventor: Johann Engelhardt, Bad Schoenborn (DE)

(73) Assignee: Leica Microsystems Heidelberg GmbH, Mannheim (DE)

( * ) Notice: Subject to any disclaimer, the term of this patent is extended or adjusted under 35 U.S.C. 154(b) by 559 days.

(21) Appl. No.: 09/987,364

(22) Filed: Nov. 14, 2001

(65) Prior Publication Data

US 2002/0057430 A1 May 16, 2002

(30) Foreign Application Priority Data

Nov. 14, 2000 (DE) .......................................... 100 56 384

(51) Int. Cl.[7] .............................................. G01N 21/64
(52) U.S. Cl. .................................... 356/318; 250/459.1
(58) Field of Search ............................... 356/317–318, 356/417; 250/458.1–461.2; 422/82.07–82.08; 600/317

(56) References Cited

U.S. PATENT DOCUMENTS

| | | | | | |
|---|---|---|---|---|---|
| 5,294,799 A | * | 3/1994 | Aslund et al. | ............ | 250/458.1 |
| 5,308,971 A | * | 5/1994 | Pope et al. | ............ | 250/214 VT |
| 5,418,371 A | * | 5/1995 | Aslund et al. | ............ | 250/458.1 |
| 5,462,879 A | * | 10/1995 | Bentsen | ....................... | 436/136 |
| 5,796,477 A | * | 8/1998 | Teich et al. | ................. | 356/318 |
| 5,866,911 A | * | 2/1999 | Baer | ....................... | 250/458.1 |
| 5,978,083 A | * | 11/1999 | Muller | ....................... | 356/318 |
| 6,020,591 A | * | 2/2000 | Harter et al. | ............. | 250/459.1 |
| 6,081,740 A | * | 6/2000 | Gombrich et al. | .......... | 600/424 |
| 6,317,206 B1 | * | 11/2001 | Wulf | ........................... | 356/317 |
| 6,323,495 B1 | * | 11/2001 | Riedel | ..................... | 250/458.1 |
| 6,426,505 B1 | * | 7/2002 | Rao et al. | ................. | 250/458.1 |
| 6,447,724 B1 | * | 9/2002 | Jensen et al. | .............. | 422/68.1 |

FOREIGN PATENT DOCUMENTS

WO WO 95/21393 8/1995

OTHER PUBLICATIONS

*Kluwer Academic/Plenum Publishers*, $2^{nd}$ ed. 1999, Chapters 4 and 5, pp. 95–184, entitled "Principles of Fluorescence Spectroscopy" by Joseph R. Lakowicz.

* cited by examiner

*Primary Examiner*—Gregory J. Toatley, Jr.
*Assistant Examiner*—Kara Geisel
(74) *Attorney, Agent, or Firm*—Crowell & Moring LLP

(57) ABSTRACT

An apparatus for measuring the lifetime of an excited state in a specimen is disclosed. The apparatus comprises an electromagnetic energy source (1) that emits light (3) of one wavelength. Also provided are a means (5) for dividing the light (3) into at least a first and a second partial light beam (7, 9) and an intermediate element (23) in at least one partial light beam to influence the transit time.

7 Claims, 4 Drawing Sheets

METHOD AND APPARATUS FOR MEASURING THE LIFETIME OF AN EXCITED STATE IN A SPECIMEN

CROSS REFERENCE TO RELATED APPLICATIONS

This application claims priority of the German patent application 100 56 384.8-52 which is incorporated by reference herein.

FIELD OF THE INVENTION

The invention concerns a method and an apparatus for measuring the lifetime of an excited state in a specimen.

BACKGROUND OF THE INVENTION

In scanning microscopy, a sample is illuminated with a light beam in order to observe the reflected or fluorescent light emitted from the sample. The focus of the illuminating light beam is moved in a specimen plane with the aid of a controllable beam deflection device, generally by tilting two mirrors; the deflection axes are usually at right angles to one another, so that one mirror deflects in the X and the other in the Y direction. The tilting of the mirrors is brought about, for example, using galvanometer positioning elements. The power level of the light coming from the specimen is measured as a function of the position of the scanning beam. The positioning elements are usually equipped with sensors for ascertaining the present mirror position.

In confocal scanning microscopy specifically, a specimen is scanned in three dimensions with the focus of a light beam.

A confocal scanning microscope generally comprises a light source, a focusing optical system with which the light of the source is focused onto a pinhole (called the excitation stop), a beam splitter, a beam deflection device for beam control, a microscope optical system, a detection stop, and the detectors for detecting the detected or fluorescent light. The illuminating light is coupled in via a beam splitter. The fluorescent or reflected light coming from the specimen arrives via the beam deflection device back at the beam splitter, passes through it, and is then focused onto the detection stop behind which the detectors are located. Detected light that does not derive directly from the focus region takes a different light path and does not pass through the detection stop, so that a point datum is obtained which, by sequential scanning of the specimen, results in a three-dimensional image. Usually a three-dimensional image is obtained by image acquisition in layers.

The power level of the light coming from the specimen is measured at fixed time intervals during the scanning operation, and thus scanned one grid point at a time. The measured value must be unequivocally associated with the pertinent scan position so that an image can be generated from the measured data. Preferably, for this purpose the status data of the adjusting elements of the beam deflection device are also continuously measured, or (although this is less accurate) the setpoint control data of the beam deflection device are used.

In a transmitted-light arrangement it is also possible, for example, to detect the fluorescent light, or the transmission of the exciting light, on the condenser side. The detected light beam does not then pass via the scanning mirror to the detector (non-descan configuration). For detection of the fluorescent light in the transmitted-light arrangement, a condenser-side detection stop would be necessary in order to achieve three-dimensional resolution as in the case of the descan configuration described. In the case of two-photon excitation, however, a condenser-side detection stop can be omitted, since the excitation probability depends on the square of the photon density (proportional intensity$^2$), which of course is much greater at the focus than in neighboring regions. The fluorescent light to be detected therefore derives, with high probability, almost exclusively from the focus region; this makes superfluous any further differentiation between fluorescent photons from the focus region and fluorescent photons from the neighboring regions using a stop arrangement.

Arrangements that limit the resolution capability of a confocal scanning microscope are determined, among other factors, by the intensity distribution and spatial extension of the focus of the illuminating light beam. An arrangement for increasing the resolution capability for fluorescence applications is known from PCT/DE/95/00124. In this, the lateral edge regions of the illumination focus volume are illuminated with light of a different wavelength that is emitted by a second laser, so that the specimen regions excited there by the light of the first laser are brought back to the ground state in stimulated fashion. Only the light spontaneously emitted from the regions not illuminated by the second laser is then detected, the overall result being an improvement in resolution. This method has become known as STED (stimulated emission depletion).

In microscopy, specimens that, for example, have been prepared with fluorescent dyes are examined. Both one-photon excitation and multi-photon excitation are usual for the excitation of fluorescent dyes. Several different dyes that emit fluorescent light of different wavelengths are often used. The dyes are utilized in such a way that they become attached specifically to specimen constituents.

In fluorescent resonant energy transfer (FRET), fluorescent molecules are excited optically, for example with light of the 488 nm wavelength. The emitted light of these so-called donor molecules, which in this example would have a wavelength of approx. 543 nm, results by way of so-called Foerster transfer in the excitation of other closely adjacent molecules (the acceptor molecules). The excited state of the acceptor molecules decays first into an intermediate state and then into the ground state, emitting light at a wavelength of approx. 570 nm in the present example. In addition to excitation of the acceptor molecules by Foerster transfer, some (undesirable) direct excitation can also occur.

Concentration-independent information about the specimen can be provided by way of the lifetime of the excited state of the fluorescent dyes. The lifetime of the fluorescent dyes depends, inter alia, on the nature and composition of the environment. In cell biology, for example, a measurement of the lifetime of the fluorescent dyes can provide indirect information about the calcium concentration in a specimen region.

Several methods for measuring the lifetime of the excited states of fluorescent dyes have become established. These methods are described exhaustively in Chapters 4 and 5 of the textbook by Joseph R. Lakowicz entitled "Principles of Fluorescence Spectroscopy," Kluwer Academic/Plenum Publishers, 2nd ed., 1999.

It is usual, for example, to modulate the power level of the exciting light over time in order to draw conclusions, from the phase retardation of the emitted light, as to the lifetime of the excited state. It is also usual to excite the fluorescent dye with short light pulses so that the time delay of the emitting light pulses can be measured electronically.

There are fluorescent dyes that exhibit an excited state lifetime of a few nanoseconds or even in the picosecond range. Such a short lifetime cannot be measured with the known methods, since even with complex electronics it is not possible simultaneously to achieve high time resolution and a good signal-to-noise ratio. In addition, with the aforementioned modulation methods it is extremely difficult to modulate the exciting light at high frequencies. The necessary frequencies (several hundred megahertz or even several gigahertz) cannot be achieved even with acoustooptical modulators.

SUMMARY OF THE INVENTION

It is therefore the object of the invention to propose a method for measuring the lifetime of an excited state of a specimen that solves the aforesaid problems.

A method of this kind is characterized by the following steps:

generating an exciting light pulse and an emitting light pulse;

illuminating the specimen with the exciting light pulse;

illuminating the specimen with the emitting light pulse at a predefined time offset from illuminating the specimen with the exciting light pulse;

detecting the power level of the luminescent light emerging from the specimen;

repeating the first four steps with different time offsets; and determining the lifetime of the excited state of the specimen as a function of the power level of the luminescent light emerging from the specimen and the time offset.

A further object of the invention is to describe an apparatus which allows lifetime measurements of excited states in a specimen and solves the drawbacks of the prior art.

An apparatus of this kind is characterized in that the apparatus comprises an electromagnetic energy source that emits light of one wavelength, a means for dividing the light into at least a first and a second partial light beam and an intermediate element in at least one partial light beam to influence the time of travel of the at least one partial light beam.

One advantage of the invention is to describe a scanning microscope having the apparatus according to the present invention. The scanning microscope is equipped with a device for generating a relative motion between an illuminating light beam and a specimen. A microscope optical system and at least one suitable detector are additionally provided. An electromagnetic energy source emits light, and means for spatial division are placed after the electromagnetic energy source. An intermediate element for influencing the transit time is moreover provided in at least one partial light beam.

The invention has the further advantage that by the controlled use of stimulated emission, it makes superfluous techniques and methods that complicate or indeed prevent the measurement of a short excited state lifetime.

The aforementioned problems are reduced to the exact adjustment of the time offset between exciting light pulse and emitting light pulse. It is very particularly advantageous in this context if a single electromagnetic energy source, whose light serves, by division, to generate the exciting light pulse and the emitting light pulse, is provided. In this case, adjustment of the time offset is achieved by adjusting transit time differences between the divided light paths.

With the apparatus according to the present invention it is easy to ascertain whether Foerster transfer in a specimen prepared for FRET is proceeding efficiently, specifically by measuring the lifetime of the excited state of the donor. If the lifetime changes as compared to the unmodified donor lifetime, a further decay channel has been added; this allows definite conclusions to be drawn as to the efficiency of FRET excitation.

BRIEF DESCRIPTION OF THE DRAWINGS

The subject matter of the invention is depicted schematically in the drawings and described below with reference to the Figures, in which.

DETAILED DESCRIPTION OF THE INVENTION

Figure 1:
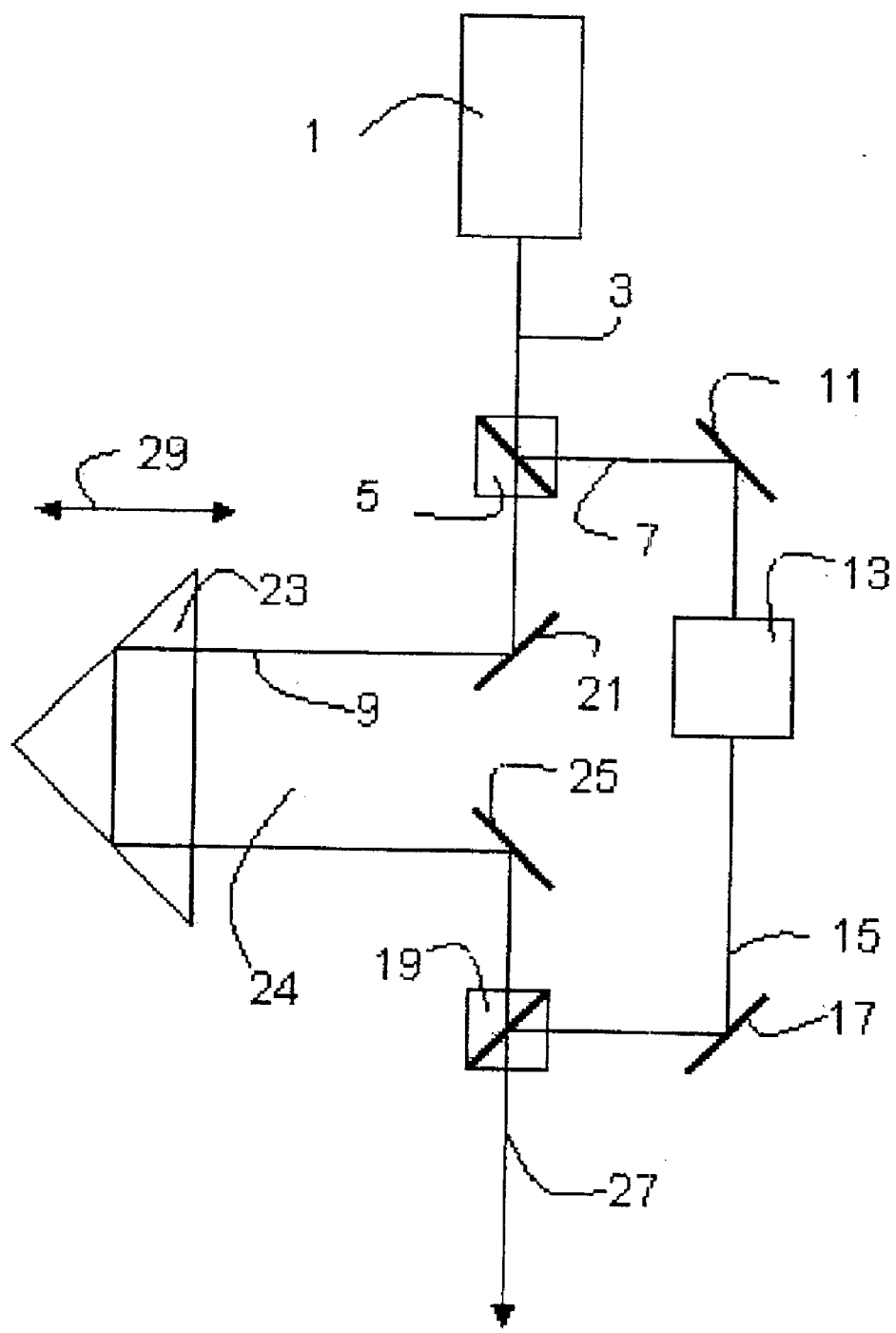
FIG. 1 shows an apparatus according to the present invention.

FIG. 1 shows an apparatus according to the present invention. A pulsed laser that is embodied as a titanium:sapphire laser is provided as electromagnetic energy source 1. Light 3 of the pulsed laser is split by beam splitter 5 into a first and a second partial light beam 9 and 7. Partial light beam 7 arrives via mirror 11 at optically parametric oscillator 13. Light beam 15 emerging from the optically parametric oscillator is guided via mirror 17 to dichroic beam combiner 19 and there combined with partial light beam 9. After beam splitting at beam splitter 5, partial light beam 9 is directed with the aid of mirror 21 onto an intermediate element 23 which is configured, for example, as a right-angle prism which is arranged in such a way that partial light beam 9 is totally reflected at the two short faces and passes perpendicularly through the hypotenuse surface. By way of mirror 25, partial beam 9 arrives at dichroic beam combiner 19. The time offset of the light pulses in combined light beam 27 can be modified by displacing prism 23 in the directions indicated by double arrow 29. Intermediate element 23 defines, in the optical path of second partial light beam 7, an optical path extension that is referred to as a "chicane" 24.

Figure 2:
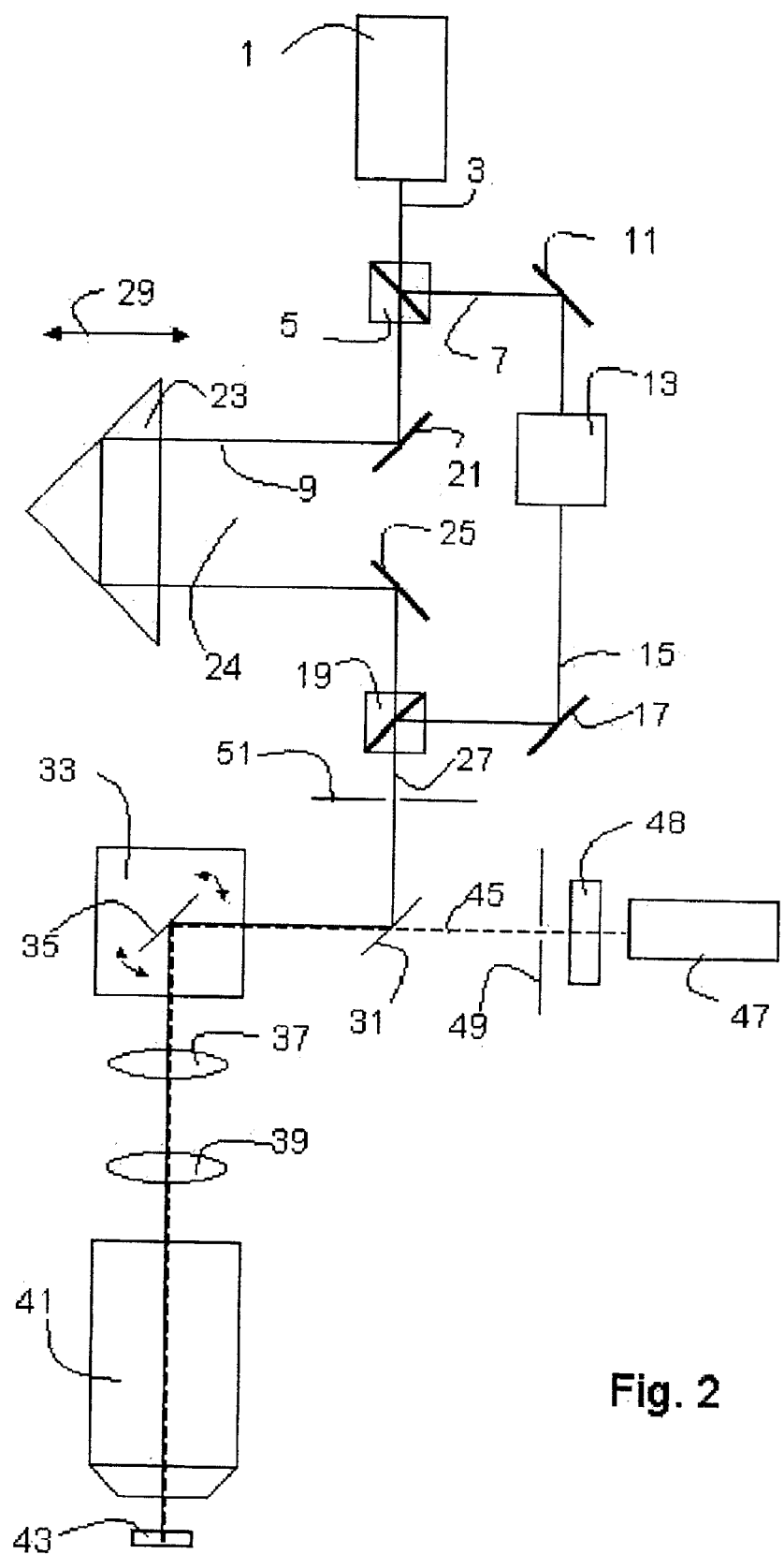
FIG. 2 shows a scanning microscope according to the present invention.

FIG. 2 shows a scanning microscope according to the present invention that is embodied as a confocal scanning microscope. The apparatus shown in FIG. 1 serves for illumination, and identical elements are thus provided with the same reference characters.

Combined light beam 27 is reflected from a beam splitter 31 to scanning module 33, which contains a gimbal-mounted scanning mirror 35 that guides combined light beam 27, via scanning optical system 37 and optical system 39 and through microscope optical system 41, over or through specimen 43. In the case of non-transparent specimens 43, combined light beam 27 is guided over the specimen surface. In the case of biological specimens 43 (preparations) or transparent specimens, combined light beam 27 can also be guided through specimen 43. This means that different focal planes of specimen 43 are also scanned successively by the light beam 3. Combined light beam 27 is depicted as a solid line. Light 45 emerging from the specimen arrives through microscope optical system 41 and via scanning module 33 at beam splitter 31, passes through the latter, and strikes detector 47, which is embodied as a photomultiplier. Light 45 emerging from specimen 43 is depicted as a dashed line. In detector 47, electrical detection signals proportional to the power level of luminescent light 45 emerging from the specimen are generated, and are forwarded to a processing unit (not depicted). Arranged in front of the detector is a bandpass filter 48 that blocks light of the wavelengths of light beam 15. Illumination pinhole 51 and detection pinhole 49, which are usually provided in a confocal scanning microscope, are depicted schematically for the sake of completeness. Certain optical elements for guiding and shaping the light beams are omitted, however, for better clarity; these are sufficiently known to those skilled in this art.

Figure 3:
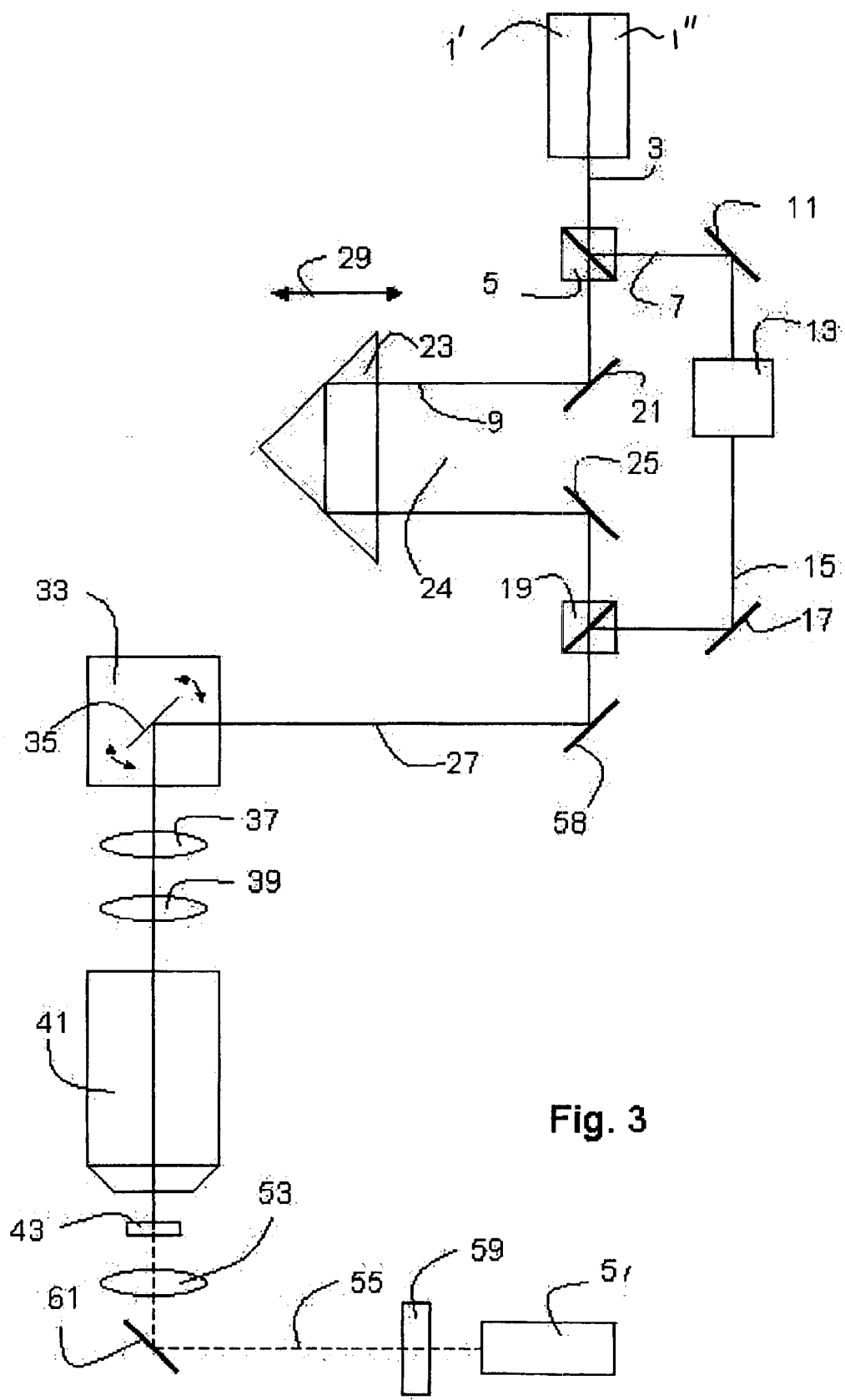
FIG. 3 shows a scanning microscope according to the present invention in a non-descan configuration and with multi-photon excitation.

FIG. 3 shows a scanning microscope according to the present invention in the non-descan configuration with multi-photon excitation. The apparatus shown in FIG. 1 serves for illumination, and identical elements are thus provided with the same reference characters.

In this embodiment, detection takes place on the condenser side. Detected light 55 emerging from specimen 43 is focused by condenser optical system 53 and directed via mirror 61 to detector 57, which is embodied as a photomultiplier. Arranged in front of the detector is a bandpass filter 59 that blocks light of the wavelength of light beam 15. The sample is illuminated in a manner analogous to that described in FIG. 2.

Figure 4:
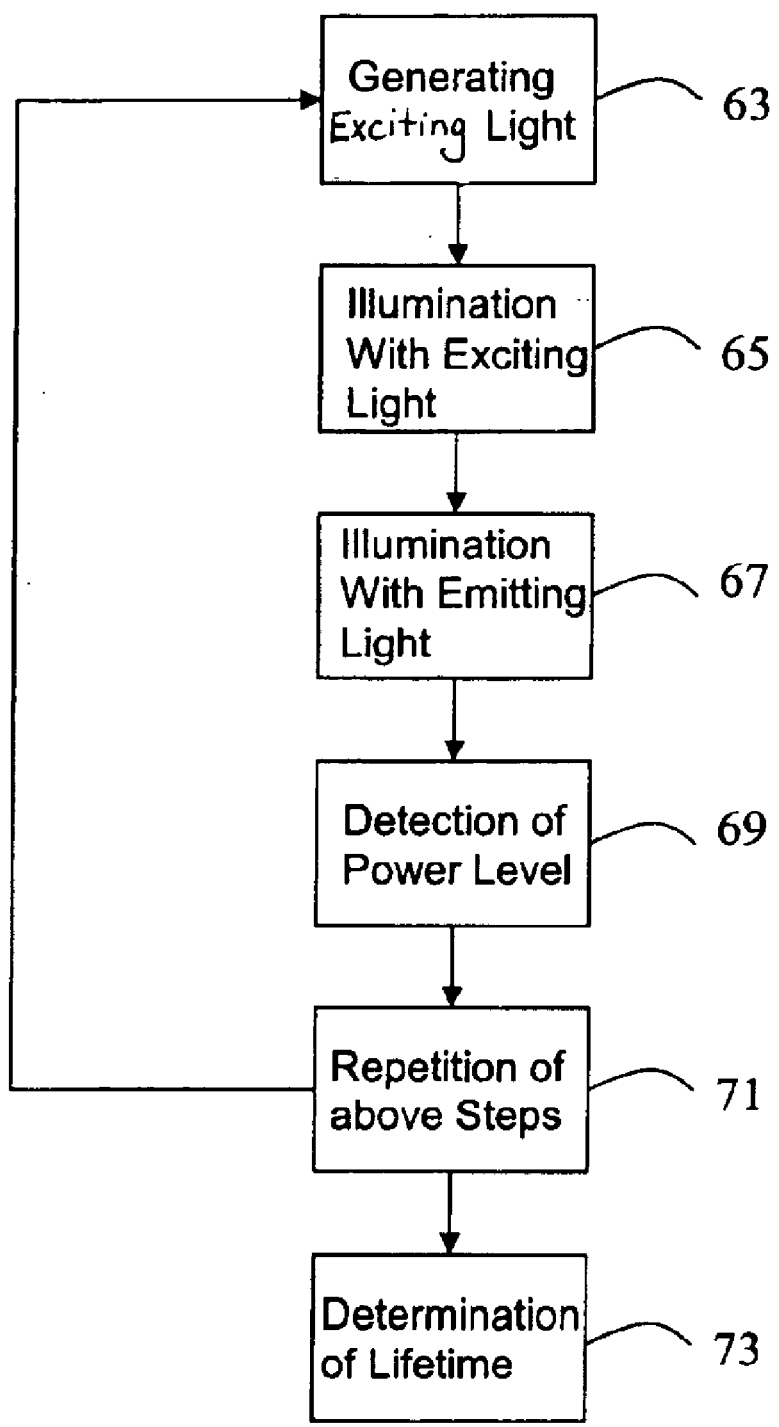
FIG. 4 shows a flow chart of the method according to the present invention.

FIG. 4 shows a flow chart of the method according to the present invention. In a first step, generation 63 of an exciting light pulse and an emitting light pulse is accomplished. A good choice for this purpose is to use mode-coupled pulsed lasers whose light is split into two partial beams. It is also possible to use two pulsed light sources (see FIG. 3, pulsed lasers 1' and 1"), but these must then emit the light pulses in a manner synchronized with one another. In a further step, illumination 65 of the specimen with the exciting light pulse is performed. The exciting light pulse can effect either one- or multi-photon excitation. The next step is illumination 67 of the specimen with the emitting light pulse at a predefined time offset from illumination with the exciting light pulse. If the emitting light pulse strikes the specimen within the lifetime of the excited state, stimulated emission is caused. If the emitting light pulse strikes the specimen later, it does not cause any stimulated emission. In the following step, detection 69 of the power level of the luminescent light emerging from the specimen is performed; the light emitted in stimulated fashion is not detected. If stimulated emission has occurred, the power level of the luminescent light is lower than if no stimulated emission took place. A colored filter that is embodied as a bandpass filter can be used to block out the light emitted in stimulated fashion. By repetition 71 of the first four steps with different time offsets, it is possible to determine the correlation between the power level of the luminescent light emerging from the specimen and the time offset between exciting light pulse and emitting light pulse. The last step is determination 73 of the lifetime of the excited state of the specimen, based on the correlation between the power level of the luminescent light emerging from the specimen and the time offset. The shortest time offset at which stimulated light emission just fails to occur corresponds to the lifetime of the excited state.

The invention was described with reference to a particular embodiment. It is nevertheless self-evident that changes and modifications can be made without thereby leaving the range of protection of the claims recited hereinafter.

What is claimed is:

1. A method for measuring the lifetime of an excited state in a specimen, comprising the following acts:

a) generating an exciting light pulse and an emitting light pulse;
   b) illuminating the specimen with the exciting light pulse;
   c) illuminating the specimen with the emitting light pulse at a predefined time offset from illuminating the specimen with the exciting light pulse;
   d) detecting the power level of the luminescent light emerging from the specimen;
   e) repeating acts a)–d) with different time offsets;
   f) reducing the energy of the emitting light pulse in proportion to the energy of the exciting light pulse; and
   g) determining the lifetime of the excited state of the specimen as a function of the power level of the luminescent light emerging from the specimen and the time offset.

2. The method as defined in claim 1, wherein the exciting light pulse is generated with a pulsed laser, and the emitting light pulse with a further pulsed laser and both pulsed lasers are synchronized with one another.

3. The method as defined in claim 1, wherein the exciting light pulse and the emitting light pulse are generated by a single pulsed laser.

4. The method as defined in claim 1, wherein an optically parametric oscillator for reducing the energy is provided in the beam path of the emitting light pulse.

5. The method as defined in claim 1, wherein the luminescent light is fluorescent light.

6. The method as defined in claim 1, wherein the specimen is a microscopic sample equipped with fluorescent dyes.

7. The method as defined in claim 1, wherein light of the wavelength of the emitting light pulse is not detected.

* * * * *